(12) United States Patent
Balek et al.

(10) Patent No.: US 8,985,429 B2
(45) Date of Patent: Mar. 24, 2015

(54) SURGICAL STAPLING DEVICE WITH ADJUNCT MATERIAL APPLICATION FEATURE

(75) Inventors: Stephen J. Balek, Springboro, OH (US); Chad P. Boudreaux, Cincinnati, OH (US); Matthew D. Holcomb, Lebanon, OH (US); Thomas W. Lytle, IV, Liberty Township, OH (US); Matthew C. Miller, Cincinnati, OH (US); Charles J. Scheib, Loveland, OH (US); Bret W. Smith, Kings Mills, OH (US); Yi-Lan Wang, Belle Mead, NJ (US); Donald F. Wilson, Jr., Raleigh, NC (US); Edward A. Rhad, Fairfield, OH (US); Kreena R. Modi, Akron, OH (US); Joseph Zavatsky, Flemington, NJ (US); Aron O. Zingman, Cambridge, MA (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 472 days.

(21) Appl. No.: 13/242,164

(22) Filed: Sep. 23, 2011

(65) Prior Publication Data

US 2013/0075451 A1  Mar. 28, 2013

(51) Int. Cl.
*A61B 17/068* (2006.01)
*A61B 17/00* (2006.01)
(Continued)

(52) U.S. Cl.
CPC ..... *A61B 17/00491* (2013.01); *A61B 17/07207* (2013.01); *A61B 2017/07271* (2013.01); *A61B 2017/07285* (2013.01); *A61B 2017/320052* (2013.01)

USPC ....... 227/180.1; 227/19; 227/176.1; 606/142; 606/219

(58) Field of Classification Search
USPC .............. 227/19, 176.1, 175.2, 178.1, 180.1; 606/139, 142, 151, 153, 219
See application file for complete search history.

(56) References Cited

U.S. PATENT DOCUMENTS

| 2,303,131 | A | 11/1942 | Morgan |
|---|---|---|---|
| 3,364,200 | A | 1/1968 | Ashton et al. |
| 3,496,940 | A | 2/1970 | Steinman |

(Continued)

FOREIGN PATENT DOCUMENTS

| CA | 481943 | 2/1947 |
|---|---|---|
| EP | 328 401 | 8/1989 |

(Continued)

OTHER PUBLICATIONS

Abstract for FR2789885.

(Continued)

*Primary Examiner* — Scott A. Smith
(74) *Attorney, Agent, or Firm* — Frost Brown Todd LLC

(57) ABSTRACT

A surgical instrument includes a handle portion, a shaft housing a firing bar, an end effector comprising an anvil, a lower jaw, and a stapling and severing assembly responsive to a longitudinal closing motion produced by the handle portion and the shaft. The lower jaw is configured to receive a removable cartridge. The cartridge includes a housing, a plurality of staples disposed in the housing, and a deck disposed over the plurality of staples. The deck defines apertures, with each aperture being substantially disposed over each staple. The cartridge further includes an agent. The firing bar is operable to assist with releasing the agent onto a severed line of tissue when the firing bar is advanced.

19 Claims, 11 Drawing Sheets

(51) Int. Cl.
*A61B 17/072* (2006.01)
*A61B 17/32* (2006.01)

(56) References Cited

U.S. PATENT DOCUMENTS

| | | |
|---|---|---|
| 3,526,228 A | 9/1970 | Lyng |
| 4,222,383 A | 9/1980 | Schossow |
| 4,513,746 A | 4/1985 | Aranyi et al. |
| 4,549,545 A | 10/1985 | Levy |
| 4,610,250 A | 9/1986 | Green |
| 4,693,720 A | 9/1987 | Scharnberg et al. |
| 4,805,823 A | 2/1989 | Rothfuss |
| 5,011,493 A | 4/1991 | Belykh et al. |
| 5,064,057 A | 11/1991 | Iwatsuki et al. |
| 5,263,629 A | 11/1993 | Trumbull et al. |
| 5,282,829 A | 2/1994 | Hermes |
| 5,297,324 A | 3/1994 | Su |
| 5,327,914 A | 7/1994 | Shlain |
| 5,366,480 A | 11/1994 | Corriveau et al. |
| 5,383,904 A | 1/1995 | Totakura et al. |
| 5,393,594 A | 2/1995 | Koyfman et al. |
| 5,411,193 A | 5/1995 | Culp |
| 5,415,334 A | 5/1995 | Williamson, IV et al. |
| 5,465,895 A | 11/1995 | Knodel et al. |
| 5,466,462 A | 11/1995 | Rosenthal et al. |
| 5,496,603 A | 3/1996 | Riedel et al. |
| 5,503,638 A | 4/1996 | Cooper et al. |
| 5,542,594 A | 8/1996 | McKean et al. |
| 5,565,210 A | 10/1996 | Rosenthal et al. |
| 5,597,107 A | 1/1997 | Knodel et al. |
| 5,607,590 A | 3/1997 | Shimizu |
| 5,607,686 A | 3/1997 | Totakura et al. |
| 5,632,432 A | 5/1997 | Schulze et al. |
| 5,639,851 A | 6/1997 | Bezwada et al. |
| 5,641,566 A | 6/1997 | Kranzler et al. |
| 5,644,002 A | 7/1997 | Cooper et al. |
| 5,673,840 A | 10/1997 | Schulze et al. |
| 5,690,675 A | 11/1997 | Sawyer et al. |
| 5,704,534 A | 1/1998 | Huitema et al. |
| 5,711,958 A | 1/1998 | Cohn et al. |
| 5,733,308 A | 3/1998 | Daugherty et al. |
| 5,749,968 A | 5/1998 | Melanson et al. |
| 5,752,965 A | 5/1998 | Francis et al. |
| 5,755,778 A | 5/1998 | Kleshinski |
| 5,766,188 A | 6/1998 | Igaki |
| 5,769,892 A | 6/1998 | Kingwell |
| 5,810,855 A | 9/1998 | Rayburn et al. |
| 5,814,055 A | 9/1998 | Knodel et al. |
| 5,814,057 A | 9/1998 | Oi et al. |
| 5,843,096 A | 12/1998 | Igaki et al. |
| 5,902,312 A | 5/1999 | Frater et al. |
| 5,997,895 A | 12/1999 | Narotam et al. |
| 6,019,791 A | 2/2000 | Wood |
| 6,031,148 A | 2/2000 | Hayes et al. |
| 6,099,551 A | 8/2000 | Gabbay |
| 6,174,333 B1 | 1/2001 | Kadiyala et al. |
| 6,203,564 B1 | 3/2001 | Hutton et al. |
| 6,245,081 B1 | 6/2001 | Bowman et al. |
| 6,273,897 B1 | 8/2001 | Dalessandro et al. |
| 6,277,397 B1 | 8/2001 | Shimizu |
| 6,312,474 B1 | 11/2001 | Francis et al. |
| 6,325,810 B1 | 12/2001 | Hamilton et al. |
| 6,355,699 B1 | 3/2002 | Vyakarnam et al. |
| 6,488,197 B1 | 12/2002 | Whitman |
| 6,495,127 B1 | 12/2002 | Wallace et al. |
| 6,511,748 B1 | 1/2003 | Barrows |
| 6,592,597 B2 | 7/2003 | Grant et al. |
| 6,638,285 B2 | 10/2003 | Gabbay |
| 6,656,193 B2 | 12/2003 | Grant et al. |
| 6,704,210 B1 | 3/2004 | Myers |
| 6,814,741 B2 | 11/2004 | Bowman et al. |
| 6,835,336 B2 | 12/2004 | Watt |
| 6,921,412 B1 | 7/2005 | Black et al. |
| 6,962,594 B1 | 11/2005 | Thevenet |
| 6,964,363 B2 | 11/2005 | Wales et al. |
| 6,978,921 B2 | 12/2005 | Shelton, IV et al. |
| 6,988,649 B2 | 1/2006 | Shelton, IV et al. |
| 7,000,818 B2 | 2/2006 | Shelton, IV et al. |
| 7,048,755 B2 | 5/2006 | Bonutti et al. |
| 7,084,082 B1 | 8/2006 | Shimizu |
| 7,111,769 B2 | 9/2006 | Wales et al. |
| 7,143,923 B2 | 12/2006 | Shelton, IV et al. |
| 7,147,138 B2 | 12/2006 | Shelton, IV |
| 7,207,471 B2 | 4/2007 | Heinrich et al. |
| 7,211,093 B2 | 5/2007 | Sauer et al. |
| 7,268,205 B2 | 9/2007 | Williams et al. |
| 7,303,108 B2 | 12/2007 | Shelton, IV |
| 7,335,212 B2 | 2/2008 | Edoga et al. |
| 7,367,485 B2 | 5/2008 | Shelton, IV et al. |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,431,730 B2 * | 10/2008 | Viola .......................... 606/219 |
| 7,434,715 B2 | 10/2008 | Shelton, IV et al. |
| 7,434,717 B2 * | 10/2008 | Shelton et al. ............. 227/176.1 |
| 7,455,208 B2 | 11/2008 | Wales et al. |
| 7,517,356 B2 | 4/2009 | Heinrich |
| 7,559,937 B2 * | 7/2009 | de la Torre et al. ........... 606/142 |
| 7,607,557 B2 | 10/2009 | Shelton, IV et al. |
| 7,708,180 B2 | 5/2010 | Murray et al. |
| 7,721,930 B2 | 5/2010 | McKenna et al. |
| 7,738,971 B2 | 6/2010 | Swayze et al. |
| 7,845,533 B2 | 12/2010 | Marczyk et al. |
| 7,950,561 B2 * | 5/2011 | Aranyi ........................ 227/175.1 |
| 8,016,177 B2 * | 9/2011 | Bettuchi et al. ............. 227/176.1 |
| 8,016,178 B2 * | 9/2011 | Olson et al. ................. 227/178.1 |
| 8,070,036 B1 * | 12/2011 | Knodel ........................ 227/178.1 |
| 8,083,119 B2 * | 12/2011 | Prommersberger ........ 227/175.1 |
| 8,157,151 B2 * | 4/2012 | Ingmanson et al. ........ 227/176.1 |
| 8,186,558 B2 * | 5/2012 | Sapienza ..................... 227/180.1 |
| 8,210,414 B2 * | 7/2012 | Bettuchi et al. ............. 227/176.1 |
| 8,215,531 B2 | 7/2012 | Shelton, IV et al. |
| 8,231,043 B2 * | 7/2012 | Tarinelli et al. ............. 227/180.1 |
| 8,474,677 B2 * | 7/2013 | Woodard et al. ............ 227/176.1 |
| 8,678,263 B2 * | 3/2014 | Viola .......................... 227/175.1 |
| 2002/0165559 A1 | 11/2002 | Grant et al. |
| 2003/0120284 A1 | 6/2003 | Palacios et al. |
| 2003/0183671 A1 | 10/2003 | Mooradian et al. |
| 2004/0093024 A1 | 5/2004 | Lousararian et al. |
| 2004/0167572 A1 | 8/2004 | Roth et al. |
| 2004/0254608 A1 | 12/2004 | Huitema et al. |
| 2005/0042250 A1 | 2/2005 | Damien et al. |
| 2005/0059996 A1 | 3/2005 | Bauman et al. |
| 2005/0070929 A1 | 3/2005 | Dalessandro et al. |
| 2005/0101834 A1 | 5/2005 | Merade |
| 2005/0107810 A1 | 5/2005 | Morales et al. |
| 2005/0145671 A1 | 7/2005 | Viola |
| 2005/0154403 A1 | 7/2005 | Sauer et al. |
| 2005/0245965 A1 | 11/2005 | Orban, III et al. |
| 2005/0249772 A1 | 11/2005 | Malaviya et al. |
| 2005/0251153 A1 | 11/2005 | Sakamoto et al. |
| 2005/0283256 A1 | 12/2005 | Sommerich et al. |
| 2005/0288767 A1 | 12/2005 | Kujawski et al. |
| 2006/0004388 A1 | 1/2006 | Whayne et al. |
| 2006/0004407 A1 | 1/2006 | Hiles et al. |
| 2006/0047312 A1 | 3/2006 | Olmo et al. |
| 2006/0093655 A1 | 5/2006 | Bar et al. |
| 2006/0094318 A1 | 5/2006 | Matsuda et al. |
| 2006/0135992 A1 | 6/2006 | Bettuchi et al. |
| 2006/0173470 A1 | 8/2006 | Oray et al. |
| 2006/0212069 A1 | 9/2006 | Shelton, IV |
| 2006/0229672 A1 | 10/2006 | Forsberg |
| 2006/0265006 A1 | 11/2006 | White et al. |
| 2006/0265007 A1 | 11/2006 | White et al. |
| 2007/0016227 A1 | 1/2007 | de la Torre et al. |
| 2007/0034667 A1 | 2/2007 | Holsten et al. |
| 2007/0034669 A1 | 2/2007 | de la Torre et al. |
| 2007/0049953 A2 | 3/2007 | Shimoji et al. |
| 2007/0060932 A1 | 3/2007 | Stack et al. |
| 2007/0066981 A1 | 3/2007 | Meagher |
| 2007/0112360 A1 | 5/2007 | De Deyne et al. |
| 2007/0128243 A1 | 6/2007 | Serafica et al. |
| 2007/0131732 A1 | 6/2007 | Holsten et al. |

(56) References Cited

U.S. PATENT DOCUMENTS

| | | |
|---|---|---|
| 2007/0150002 A1 | 6/2007 | Szabo et al. |
| 2007/0156140 A1 | 7/2007 | Baily |
| 2007/0190108 A1 | 8/2007 | Datta et al. |
| 2007/0207180 A1 | 9/2007 | Tanihara et al. |
| 2007/0213522 A1 | 9/2007 | Harris et al. |
| 2007/0219571 A1 | 9/2007 | Balbierz et al. |
| 2007/0225642 A1 | 9/2007 | Houser et al. |
| 2007/0243227 A1 | 10/2007 | Gertner |
| 2007/0246505 A1 | 10/2007 | Pace-Floridia et al. |
| 2007/0286892 A1 | 12/2007 | Herzberg et al. |
| 2008/0039871 A1 | 2/2008 | Wallace et al. |
| 2008/0077131 A1 | 3/2008 | Yates |
| 2008/0078800 A1 | 4/2008 | Hess et al. |
| 2008/0078801 A1 | 4/2008 | Shelton, IV et al. |
| 2008/0078802 A1 | 4/2008 | Hess et al. |
| 2008/0078803 A1 | 4/2008 | Shelton, IV et al. |
| 2008/0078804 A1 | 4/2008 | Shelton, IV et al. |
| 2008/0078805 A1 | 4/2008 | Omaits et al. |
| 2008/0078806 A1 | 4/2008 | Omaits et al. |
| 2008/0078807 A1 | 4/2008 | Hess et al. |
| 2008/0081881 A1 | 4/2008 | Swetlin et al. |
| 2008/0082124 A1 | 4/2008 | Hess et al. |
| 2008/0082126 A1 | 4/2008 | Murray et al. |
| 2008/0110958 A1* | 5/2008 | McKenna et al. ........... 227/176.1 |
| 2008/0110959 A1 | 5/2008 | Orban, III et al. |
| 2008/0114381 A1 | 5/2008 | Voegele et al. |
| 2008/0114385 A1 | 5/2008 | Byrum et al. |
| 2008/0114399 A1 | 5/2008 | Bonutti |
| 2008/0125812 A1 | 5/2008 | Zubik et al. |
| 2008/0128469 A1 | 6/2008 | Dalessandro et al. |
| 2008/0140115 A1 | 6/2008 | Stopek |
| 2008/0200949 A1 | 8/2008 | Hiles et al. |
| 2008/0314960 A1 | 12/2008 | Marczyk et al. |
| 2009/0001122 A1 | 1/2009 | Prommersberger et al. |
| 2009/0076510 A1 | 3/2009 | Bell et al. |
| 2009/0078739 A1* | 3/2009 | Viola .......................... 227/180.1 |
| 2009/0118747 A1 | 5/2009 | Bettuchi et al. |

FOREIGN PATENT DOCUMENTS

| | | |
|---|---|---|
| EP | 0 667 119 | 8/1995 |
| EP | 0 781 564 | 7/1997 |
| EP | 0 818 470 | 1/1998 |
| EP | 1 098 024 | 5/2001 |
| EP | 1 229 841 | 8/2002 |
| EP | 1 494 596 | 1/2005 |
| EP | 1 621 141 | 2/2006 |
| EP | 1 647 286 | 4/2006 |
| EP | 1 759 640 | 3/2007 |
| EP | 1 836 974 | 9/2007 |
| EP | 2 039 308 | 3/2009 |
| FR | 2 789 885 | 8/2000 |
| FR | 2 850 281 | 7/2004 |
| GB | 222 954 | 10/1924 |
| GB | 493 459 | 10/1938 |
| GB | 913 218 | 12/1962 |
| JP | 107 2740 | 3/1989 |
| JP | 3146773 | 6/1991 |
| JP | 5076586 | 3/1993 |
| JP | 11309151 | 11/1999 |
| WO | WO 93/10731 | 6/1993 |
| WO | WO 98/38923 | 9/1998 |
| WO | WO 01/17446 | 3/2001 |
| WO | WO 01/62158 | 8/2001 |
| WO | WO 02/09593 | 2/2002 |
| WO | WO 02/22184 | 3/2002 |
| WO | WO 03/094743 | 11/2003 |
| WO | WO 2004/060425 | 7/2004 |
| WO | WO 2006/081174 | 8/2006 |
| WO | WO 2006/106269 | 10/2006 |
| WO | WO 2007/067621 | 6/2007 |
| WO | WO 2008/057281 | 5/2008 |

OTHER PUBLICATIONS

Abstract for FR2850281.
Abstract for JP1072740.
Abstract for JP11309151.
Abstract for JP3146773.
Abstract for JP5076586.
International Preliminary Report on Patentability dated Mar. 25, 2014 for Application No. PCT/US2012/056066.

* cited by examiner

SURGICAL STAPLING DEVICE WITH ADJUNCT MATERIAL APPLICATION FEATURE

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through a cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in; U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,964,363, entitled "Surgical Stapling Instrument having Articulation Joint Support Plates for Supporting a Firing Bar," issued Nov. 15, 2005; U.S. Pat. No. 6,978,921, entitled "Surgical Stapling Instrument Incorporating an E-Beam Firing Mechanism," issued Dec. 27, 2005; U.S. Pat. No. 6,988,649, entitled "Surgical Stapling Instrument Having a Spent Cartridge Lockout," issued Jan. 24, 2006; U.S. Pat. No. 7,000,818, entitled "Surgical Stapling Instrument Having Separate Distinct Closing and Firing Systems," issued Feb. 21, 2006; U.S. Pat. No. 7,111,769, entitled "Surgical Instrument Incorporating an Articulation Mechanism having Rotation about the Longitudinal Axis," issued Sep. 26, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument having Multistroke Firing with Opening Lockout," issued Oct. 14, 2008; U.S. Pat. No. 7,721,930, entitled "Disposable Cartridge with Adhesive for Use with a Stapling Device," issued May 25, 2010; and U.S. Pat. No. 7,455,208, entitled "Surgical Instrument with Articulating Shaft with Rigid Firing Bar Supports," issued Nov. 25, 2008. The disclosure of each of the above-cited U.S. Patents is incorporated by reference herein. While the surgical staplers referred to above are described as being used in endoscopic procedures, it should be understood that such surgical staplers may also be used in open procedures and/or other non-endoscopic procedures.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1A:
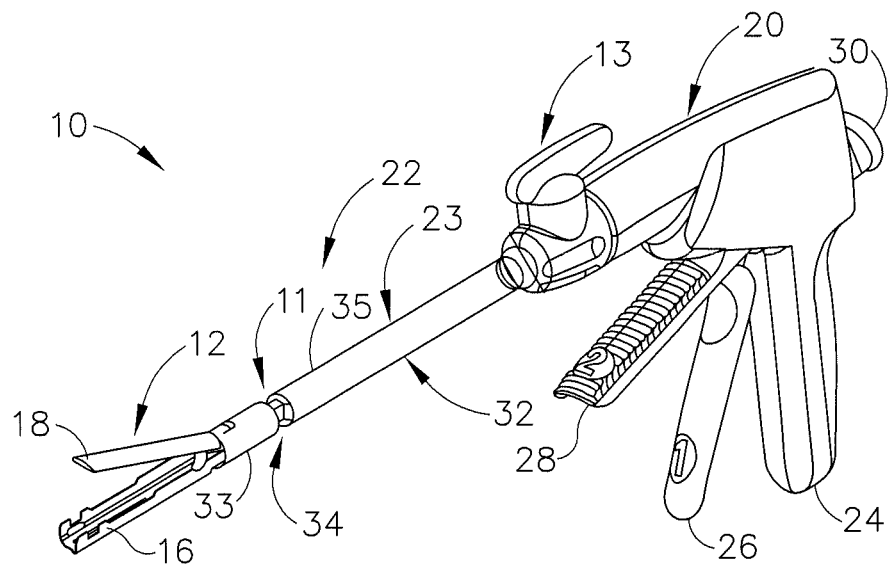
FIG. 1A depicts a perspective view of an articulating surgical instrument with an end effector in a nonarticulated position.
Figure 1B:
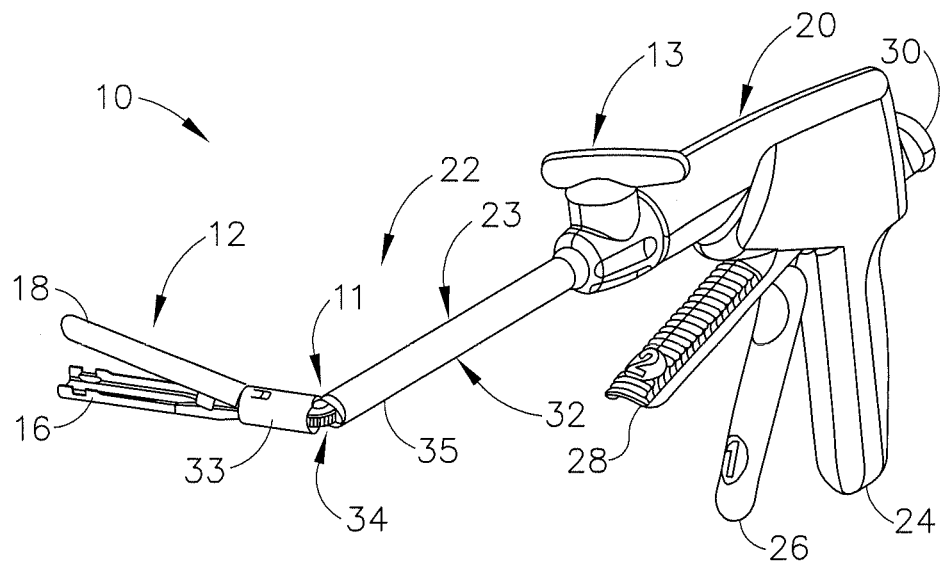
FIG. 1B depicts a perspective view of the surgical instrument of FIG. 1A with an end effector in an articulated position.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Surgical Stapler

FIGS. 1-6 depict an exemplary surgical stapling and severing instrument (10) that is sized for insertion, in a nonarticulated state as depicted in FIG. 1A, through a trocar cannula passageway to a surgical site in a patient for performing a surgical procedure. Surgical stapling and severing instrument (10) includes handle portion (20) connected to implement portion (22), the latter further comprising shaft (23) distally terminating in an articulation mechanism (11) and a distally attached end effector (12). Once articulation mechanism (11) and end effector (12) are inserted through the cannula passageway of a trocar, articulation mechanism (11) may be remotely articulated, as depicted in FIG. 1B, by articulation control (13). Thereby, end effector (12) may reach behind an organ or approach tissue from a desired angle or for other reasons. It should be understood that terms such as "proximal" and "distal" are used herein with reference to a clinician gripping handle portion (20) of instrument (10). Thus, end effector (12) is distal with respect to the more proximal handle portion (20). It will be further appreciated that for convenience and clarity, spatial terms such as "vertical" and "horizontal" are used herein with respect to the drawings. However, surgical instruments are used in many orientations and positions, and these terms are not intended to be limiting and absolute.

End effector (12) of the present example includes a lower jaw (16) and a pivotable anvil (18). Handle portion (20) includes pistol grip (24) toward which closure trigger (26) is pivotally drawn by the clinician to cause clamping, or closing, of the anvil (18) toward lower jaw (16) of end effector (12). Such closing of anvil (18) is provided through an outmost closure sleeve (32), which longitudinally translates relative to handle portion (20) in response to pivoting of closure trigger (26) relative to pistol grip (24). A distal closure ring (33) of closure sleeve (32) is indirectly supported by frame (34) of implement portion (22). At articulation mechanism (11), a proximal closure tube (35) of closure sleeve (32) communicates with the distal closure ring (33). Frame (34) is flexibly attached to lower jaw (16) via articulation mechanism (11), enabling articulation in a single plane. Frame (34) also longitudinally slidingly supports a firing drive member (not shown) that extends through shaft (23) and communicates a firing motion from firing trigger (28) to firing bar (14). Firing trigger (28) is farther outboard of closure trigger (26) and is pivotally drawn by the clinician to cause the stapling and severing of clamped tissue in end effector (12), as will be described in greater detail below. Thereafter, release button (30) is depressed to release the tissue from end effector (12).

FIGS. 2-5 depict end effector (12) employing an E-beam firing bar (14) to perform a number of functions. As best seen in FIGS. 3A-3B, firing bar (14) includes a transversely oriented upper pin (38), a firing bar cap (44), a transversely oriented middle pin (46), and a distally presented cutting edge (48). Upper pin (38) is positioned and translatable within an anvil pocket (40) of anvil (18). Firing bar cap (44) slidably engages a lower surface of lower jaw (16) by having firing bar (14) extend through channel slot (45) (shown in FIG. 3B) that is formed through lower jaw (16). Middle pin (46) slidably engages a top surface of lower jaw (16), cooperating with firing bar cap (44). Thereby, firing bar (14) affirmatively spaces end effector (12) during firing, overcoming pinching that may occur between anvil (18) and lower jaw (16) with a minimal amount of clamped tissue and overcoming staple malformation with an excessive amount of clamped tissue.

Figure 2:
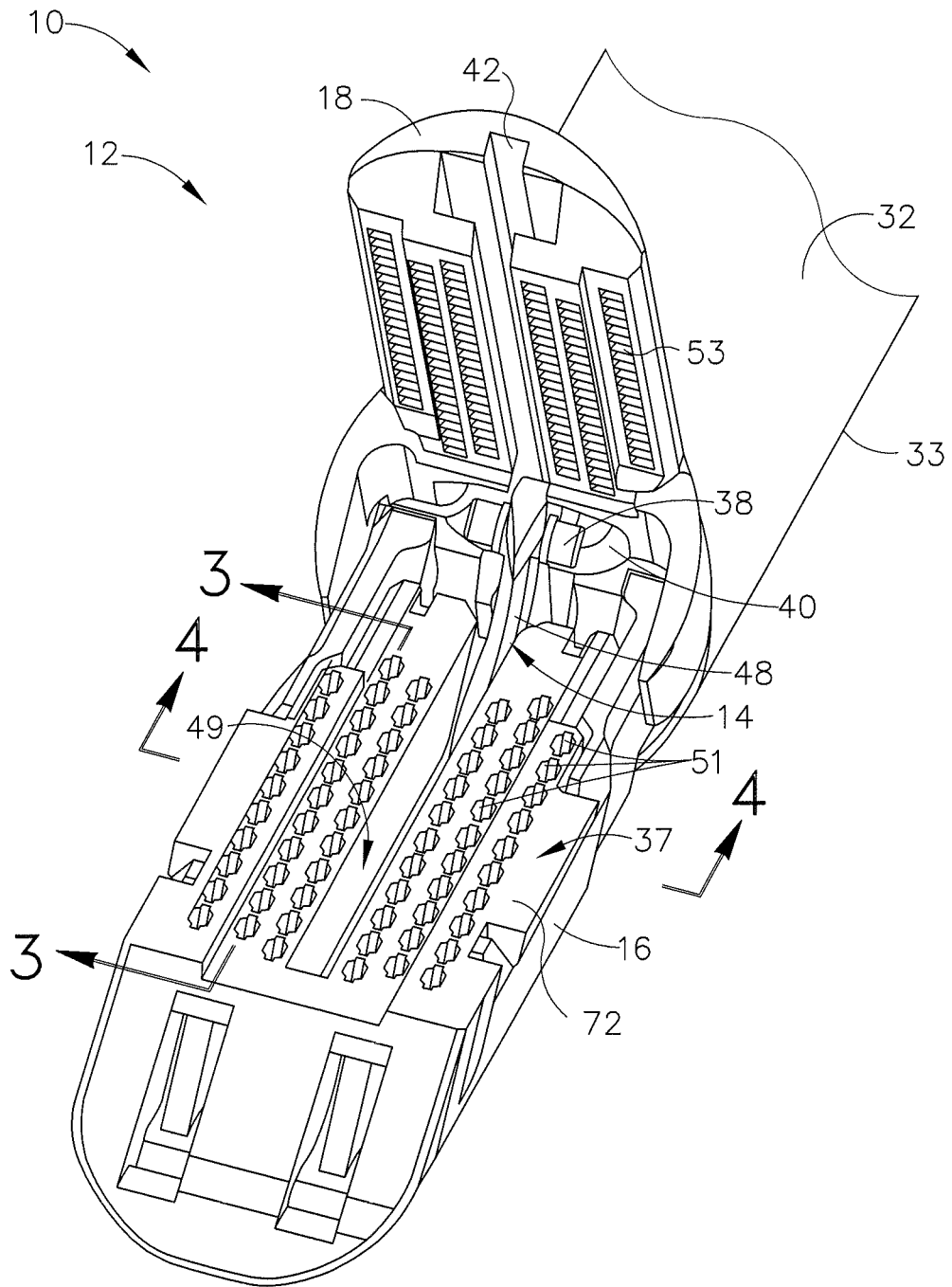
FIG. 2 depicts a perspective view of an opened end effector of the surgical instrument of FIGS. 1A-1B.
Figure 3A:
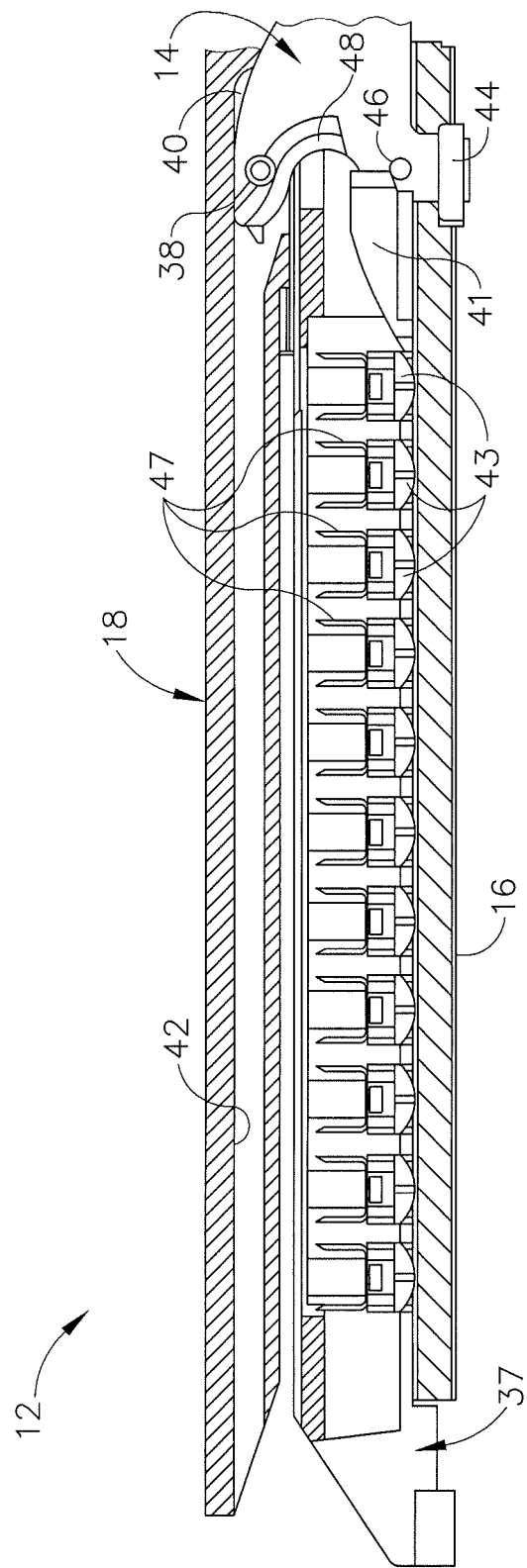
FIG. 3A depicts a side cross-sectional view of the end effector of FIG. 2, taken along line 3-3 of FIG. 2, with the firing bar in a proximal position.
Figure 3B:
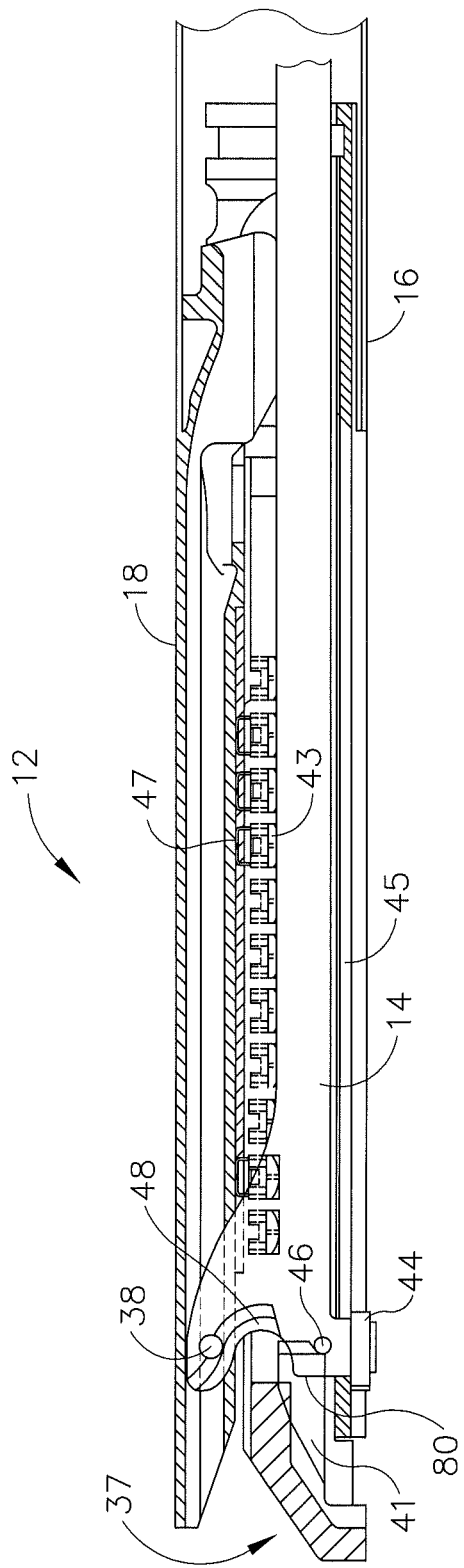
FIG. 3B depicts a side cross-sectional view of the end effector of FIG. 2, taken along line 3-3 of FIG. 2, but showing the firing bar in a distal position.
Figure 4:
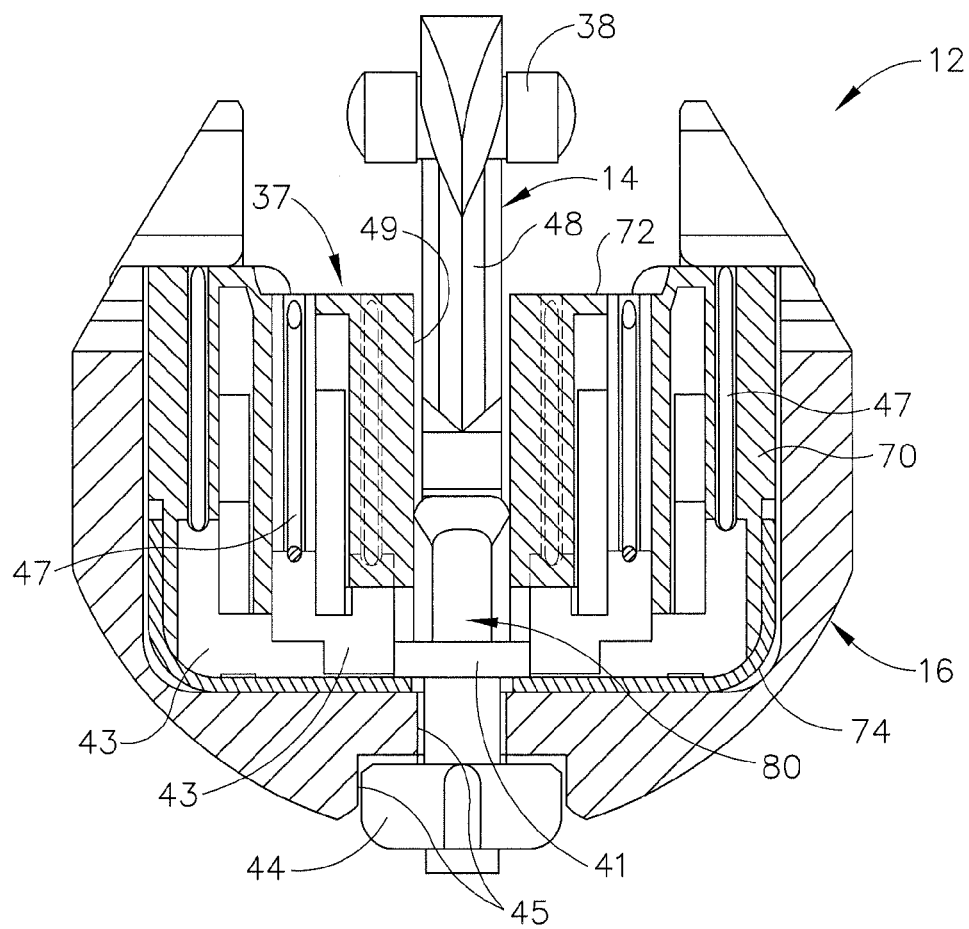
FIG. 4 depicts an end cross-sectional view of the end effector of FIG. 2, taken along line 4-4 of FIG. 2.
Figure 5:
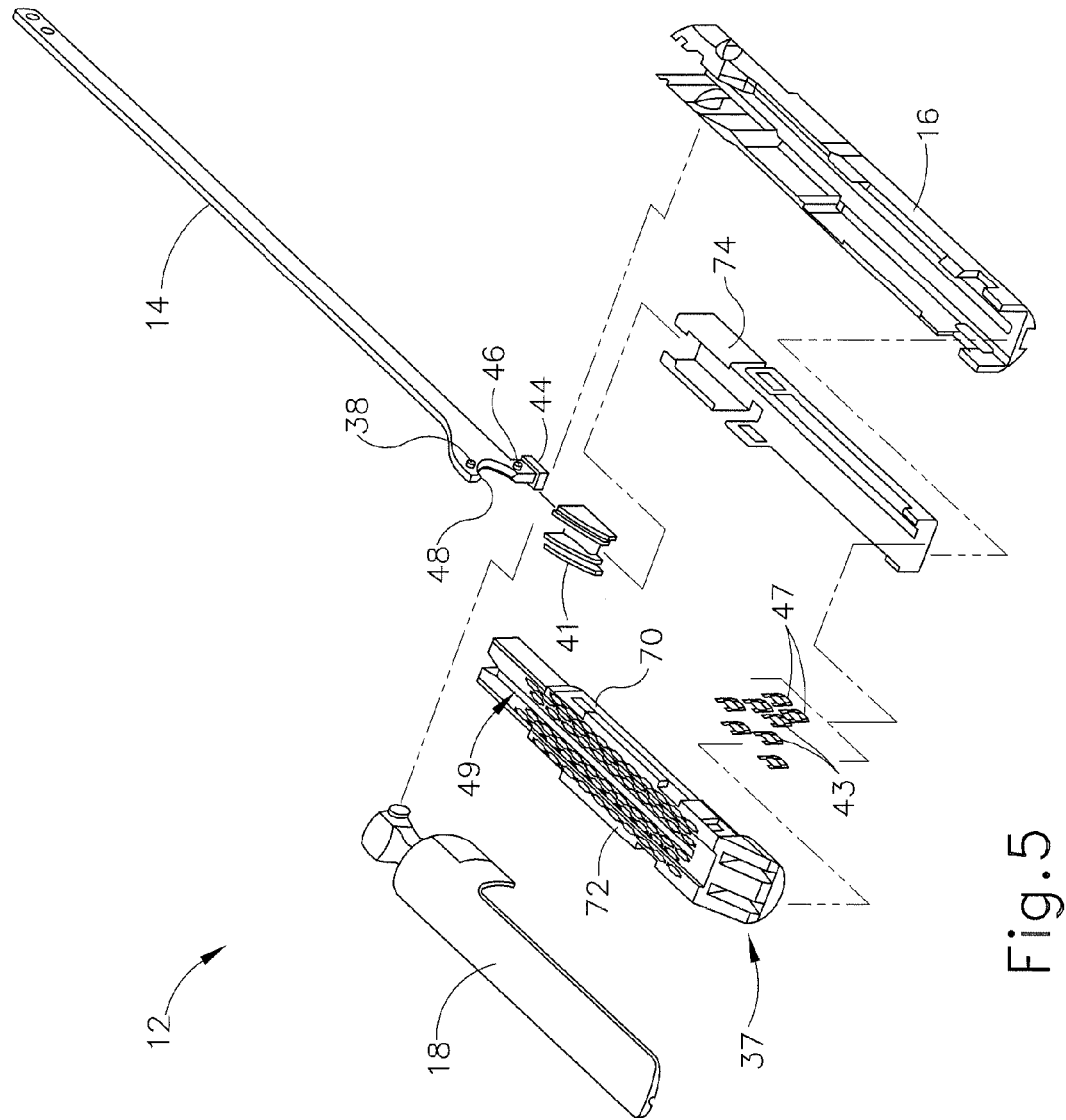
FIG. 5 depicts an exploded perspective view of the end effector of FIG. 2.

FIG. 2 shows firing bar (14) proximally positioned and anvil (18) pivoted to an open position, allowing an unspent staple cartridge (37) to be removably installed into a channel of lower jaw (16). As best seen in FIGS. 4-5, staple cartridge (37) of this example includes a cartridge body (70), which presents an upper deck (72) and is coupled with a lower cartridge tray (74). As best seen in FIG. 2, a vertical slot (49) is formed through part of staple cartridge (37). As also best seen in FIG. 2, three rows of staple apertures (51) are formed through upper deck (72) on one side of vertical slot (49), with another set of three rows of staple apertures (51) being formed through upper deck (72) on the other side of vertical slot (49). Referring back to FIGS. 3-5, a wedge sled (41) and a plurality of staple drivers (43) are captured between cartridge body (70) and tray (74), with wedge sled (41) being located proximal to staple drivers (43). Wedge sled (41) is movable longitudinally within staple cartridge (37); while staple drivers (43) are movable vertically within staple cartridge (37). Staples (47) are also positioned within cartridge body (70), above corresponding staple drivers (43). In particular, each staple (47) is driven vertically within cartridge body (70) by a staple driver (43) to drive staple (47) out through an associated staple aperture (51). As best seen in FIGS. 3A-3B and 5, wedge sled (41) presents inclined cam surfaces that urge staple drivers (43) upwardly as wedge sled (41) is driven distally through staple cartridge (37).

With end effector (12) closed as depicted in FIG. 3A, firing bar (14) is advanced in engagement with anvil (18) by having upper pin (38) enter a longitudinal anvil slot (42). A pusher block (80) is located at the distal end of firing bar (14), and is configured to engage wedge sled (41) such that wedge sled (41) is pushed distally by pusher block (80) as firing bar (14) is advanced distally through staple cartridge (37). During such firing, cutting edge (48) of firing bar (14) enters vertical slot (49) of staple cartridge (37), severing tissue clamped between staple cartridge (37) and anvil (18). As shown in FIGS. 3A-3B, middle pin (46) and pusher block (80) together actuate staple cartridge (37) by entering into slot (49) within staple cartridge (37), driving wedge sled (41) into upward camming contact with staple drivers (43) that in turn drive staples (47) out through staple apertures (51) and into forming contact with staple forming pockets (53) on the inner surface of anvil (18). FIG. 3B depicts firing bar (14) fully distally translated after completing severing and stapling tissue.

Figure 6:
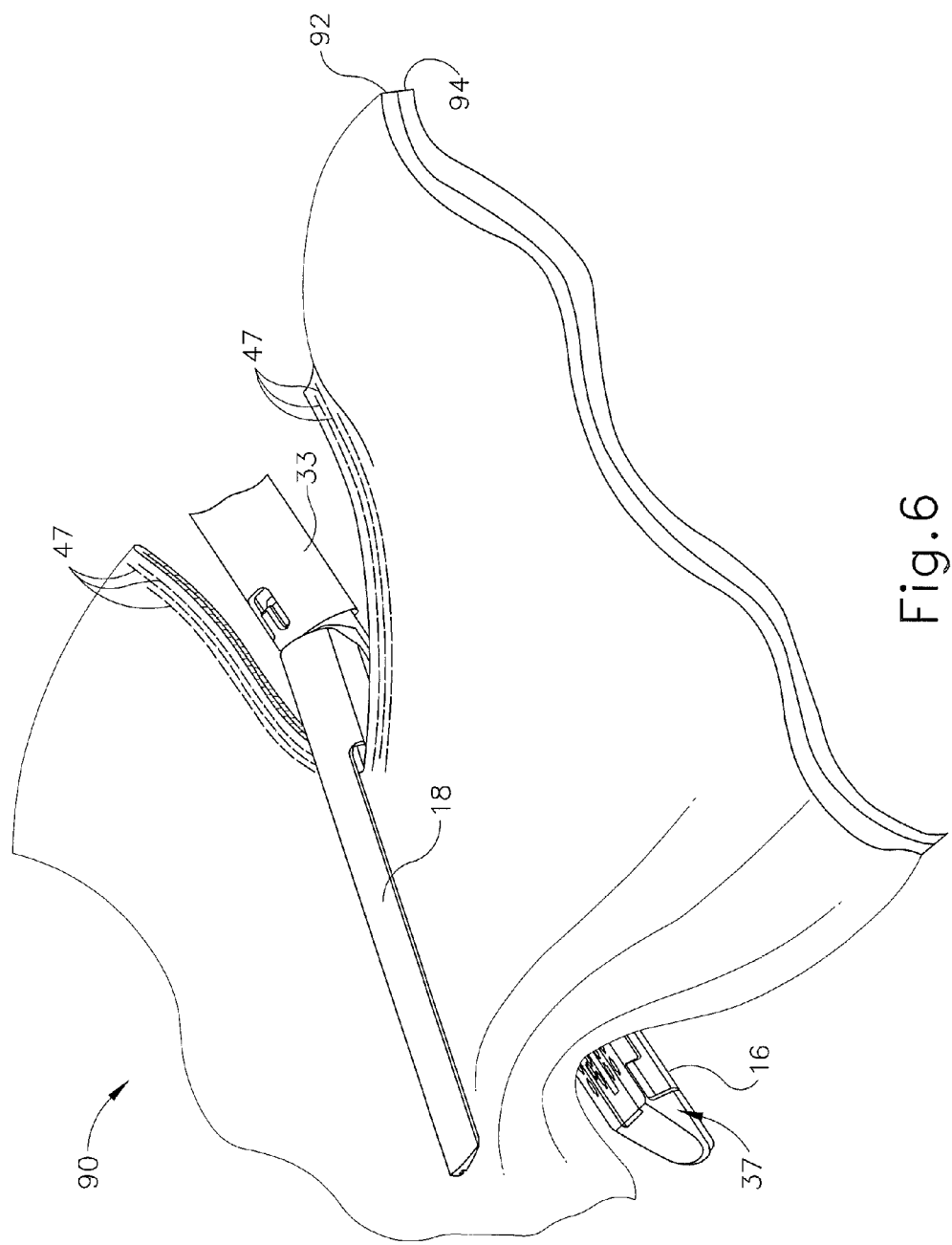
FIG. 6 depicts a perspective view of the end effector of FIG. 2, positioned at tissue and having been actuated once in the tissue.

FIG. 6 shows end effector (12) having been actuated through a single stroke through tissue (90). Cutting edge (48) has cut through tissue (90), while staple drivers (43) have driven three alternating rows of staples (47) through the tissue (90) on each side of the cut line produced by cutting edge (48). Staples (47) are all oriented substantially parallel to the cut line in this example, though it should be understood that staples (47) may be positioned at any suitable orientations. In the present example, end effector (12) is withdrawn from the trocar after the first stroke is complete, spent staple cartridge (37) is replaced with a new staple cartridge, and end effector (12) is then again inserted through the trocar to reach the stapling site for further cutting and stapling. This process may be repeated until the desired amount of cuts and staples (47) have been provided. Anvil (18) may need to be closed to facilitate insertion and withdrawal through the trocar; and anvil (18) may need to be opened to facilitate replacement of staple cartridge (37).

It should be understood that cutting edge (48) may sever tissue substantially contemporaneously with staples (47) being driven through tissue during each actuation stroke. In the present example, cutting edge (48) just slightly lags behind driving of staples (47), such that a staple (47) is driven through the tissue just before cutting edge (48) passes through the same region of tissue, though it should be understood that this order may be reversed or that cutting edge (48) may be directly synchronized with adjacent staples. While FIG. 6 shows end effector (12) being actuated in two layers (92, 94) of tissue (90), it should be understood that end effector (12) may be actuated through a single layer of tissue (90) or more than two layers (92, 94) of tissue. It should also be understood that the formation and positioning of staples (47) adjacent to the cut line produced by cutting edge (48) may substantially seal the tissue at the cut line, thereby reducing or preventing bleeding and/or leaking of other bodily fluids at the cut line. Various suitable settings and procedures in which instrument (10) may be used will be apparent to those of ordinary skill in the art in view of the teachings herein. It should be understood that instrument (10) may be configured and operable in accordance with any of the teachings of U.S. Pat. Nos. 4,805,823; 5,415,334; 5,465,895; 5,597,107; 5,632,432; 5,673,840; 5,704,534; 5,814,055; 6,978,921; 7,000,818; 7,143,923; 7,303,108; 7,367,485; 7,380,695; 7,380,696; 7,404,508; 7,434,715; and/or 7,721,930.

As noted above, the disclosures of each of those patents incorporated by reference herein. Additional exemplary modifications that may be provided for instrument (10) will be described in greater detail below. Various suitable ways in which the below teachings may be incorporated into instrument (10) will be apparent to those of ordinary skill in the art. Similarly, various suitable ways in which the below teachings may be combined with various teachings of the patents cited herein will be apparent to those of ordinary skill in the art. It should also be understood that the below teachings are not limited to instrument (10) or devices taught in the patents cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. Exemplary Firing Bar and Cartridge Assembly to Deposit Adjunct Material

Examples described below include exemplary firing bar and cartridge assemblies operable to deposit adjunct material on tissue while the firing bar severs the tissue and while staples are driven from the cartridge into the tissue. The adjunct material may comprise, for example, adjunct or hemostatic agents such as fibrin or thrombin that assist to coagulate blood and reduce the amount of bleeding at the surgical site. The hemostatic abilities of such adjuncts may also contribute to the use of such adjuncts as adhesives and sealants. The agents may substantially prevent leaks along the stapled tissue site, for example. Such adjuncts or reagents may further include but are not limited to medical fluid or buttress components such as platelet poor plasma (PPP), platelet rich plasma (PRP), starch, chitosan, alginate, fibrin, polysaccharide, cellulose, collagen, bovine collagen, gelatin-resorcin-formalin adhesive, oxidized cellulose, mussel-based adhesive, poly (amino acid), agarose, amylose, hyaluronan, polyhydroxybutyrate (PHB), hyaluronic acid, poly(vinyl pyrrolidone) (PVP), poly(vinyl alcohol) (PVA), polylactide (PLA), polyglycolide (PGA), polycaprolactone (PCL), and their copolymers, VICRYL® (Ethicon, Inc., Somerville, N.J.), MONOCRYL material, PANACRYL (Ethicon, Inc., Somerville, N.J.), and/or any other material suitable to be mixed with biological material and introduced to a wound or defect site, including combinations of materials. For example, the material may be selected from the following materials: epsilon-caprolactone glycolide, bovine pericardium, polylactic acid, polyglycolic acid, polyglactin, polydioxanone, polyglyconate, whey protein, cellulose gum, starch, gelatin, silk, nylon, polypropylene, braided polyester, polybutester, polyethylene, and/or polyetheretherketones. Other suitable compounds, materials, substances, etc., that may be used in a medical fluid or buttress will be apparent to those of ordinary skill in the art in view of the teachings herein.

Suitable adjuncts or reagents may further include but are not limited to medical fluid or buttress components, including but not limited to natural or genetically engineered absorbable polymers or synthetic absorbable polymers, or mixtures thereof. Examples of natural or genetically engineered absorbable polymers are proteins, polysaccharides and combinations thereof. Proteins include, prothrombin, thrombin, fibrinogen, fibrin, fibronectin, heparinase, Factor X/Xa, Factor VII/VIIa, Factor IX/IXa, Factor XI/XIa, Factor XII/XIIa, tissue factor, batroxobin, ancrod, ecarin, von Willebrand Factor, collagen, elastin, albumin, gelatin, platelet surface glycoproteins, vasopressin, vasopressin analogs, epinephrine, selectin, procoagulant venom, plasminogen activator inhibitor, platelet activating agents, synthetic peptides having hemostatic activity, and/or combinations thereof. Polysaccharides include, without limitation, cellulose, alkyl cellulose, e.g. methylcellulose, alkylhydroxyalkyl cellulose, hydroxyalkyl cellulose, cellulose sulfate, salts of carboxymethyl cellulose, carboxymethyl cellulose, carboxyethyl cellulose, chitin, carboxymethyl chitin, hyaluronic acid, salts of hyaluronic acid, alginate, alginic acid, propylene glycol alginate, glycogen, dextran, dextran sulfate, curdlan, pectin, pullulan, xanthan, chondroitin, chondroitin sulfates, carboxymethyl dextran, carboxymethyl chitosan, chitosan, heparin, heparin sulfate, heparan, heparan sulfate, dermatan sulfate, keratan sulfate, carrageenans, chitosan, starch, amylose, amylopectin, poly-N-glucosamine, polymannuronic acid, polyglucuronic acid polyguluronic acid, and derivatives of any of the above. Examples of synthetic absorbable polymers are aliphatic polyester polymers, copolymers, and/or combinations thereof. The aliphatic polyesters are typically synthesized in a ring opening polymerization of monomers including, but not limited to, lactic acid, lactide (including L-, D-, meso and D, L mixtures), glycolic acid, glycolide, ε-caprolactone, p-dioxanone (1,4-dioxan-2-one), and trimethylene carbonate (1,3-dioxan-2-one).

In some versions, a medical fluid may be suspended in a biocompatible carrier to form the material of the adjunct. Suitable carriers may include, for example, a physiological buffer solution, a flowable gel solution, saline, and water. In the case of gel solutions, the tissue repair composition may be in a flowable gel form prior to delivery at the target site, or may form a gel and remain in place after delivery at the target site. Flowable gel solutions may comprise one or more gelling materials with or without added water, saline, or a physiological buffer solution. Suitable gelling materials include biological and synthetic materials. Exemplary gelling materials include proteins, polysaccharides, polynucleotides, and other materials such as alginate, cross-linked alginate, poly (N-isopropylacrylamide), poly(oxyalkylene), copolymers of poly(ethylene oxide)-poly(propylene oxide), poly(vinyl alcohol), polyacrylate, or monostearoyl glycerol co-Succinate/polyethylene glycol (MGSA/PEG) copolymers, and combinations of any of the foregoing.

The material may further be retained in and/or comprise a fibrous pad, a foam, a matrix, a mesh, or another structure, in accordance with the teachings of, by way of example, U.S. Patent App. Pub. No. 2009/0120994, entitled "Surgical Fastening Device with Initiator Impregnation of a Matrix or Buttress to Improve Adhesive Application", published May 14, 2009, issued as U.S. Pat. No. 7,708,180 on May 4, 2010, the disclosure of which is incorporated by reference herein. The material may comprise, for example, a biocompatible material that is a buttress, a matrix having a plurality of openings therein, an open cell or closed cell foam, and/or a fabric pad. The material may include porosities that induce a wicking feature to drawing adhesive into the material and ensure the openings remain clear of the adhesive, allowing tissue growth through the openings after application to tissue.

Additionally or alternatively, the adjunct material may be comprised of an adhesive such as, but not limited to, polymerizable and/or cross-linkable materials such as a cyanoacrylate adhesive. The adhesive, for example, may be a monomeric (including prepolymeric) adhesive composition, a polymeric adhesive composition, or any other compound that can adhere to tissue. In embodiments, the monomer may be a 1,1-disubstituted ethylene monomer, e.g., an alpha-cyanoacrylate. When cross linked or polymerized, the cyanoacrylate can change from a liquid to a solid. Polymerized adhesives for example, can be formulated to be flexible to rigid and could be spongy. If desired, the adhesive can be a single part or dual part adhesive, and/or can contain additives such as alternate compounds. Polymerization of the adhesive can occur from, but is not limited to, exposure to moisture, heat, and/or adhesion initiators such as those described in U.S. Patent App. Pub. No. 2009/0120994, issued as U.S. Pat. No. 7,708,180 on May 4, 2010, the disclosure of which is incorporated by reference above. Other suitable materials and compositions that may be used will be apparent to those of ordinary skill in the art in view of the teachings herein.

A. Top Notch on Firing Bar Version

Figure 7:
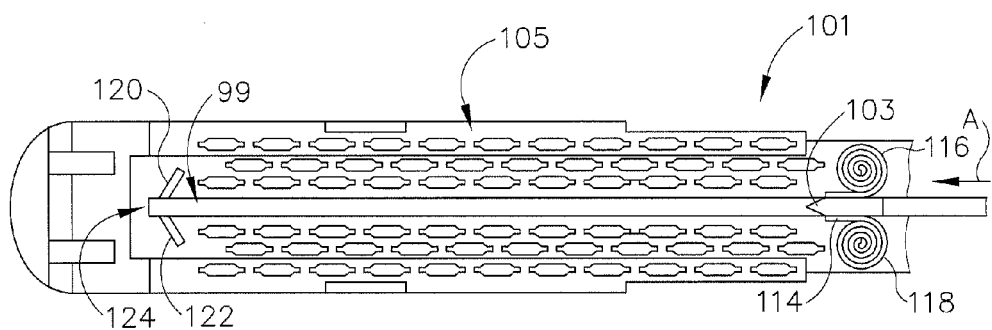
FIG. 7 depicts a plan view of a version of an exemplary removable cartridge of the end effector of FIG. 2 and an exemplary firing bar with an adjunct material connected to the firing bar, with the firing bar in a first position.
Figure 8:
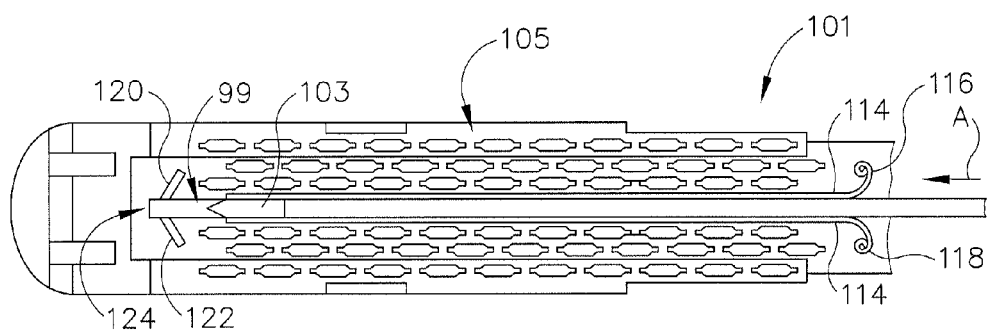
FIG. 8 depicts a plan view of the cartridge of FIG. 7 with the firing bar in a second position.
Figure 9:
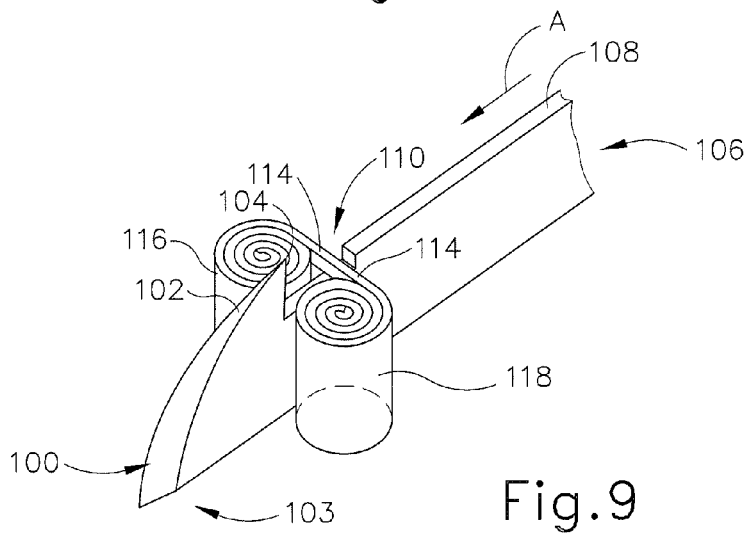
FIG. 9 depicts a fragmentary, perspective view of the adjunct material of FIG. 7 captured in a top notch in the firing bar of FIG. 7.

FIGS. 7-8 show a removable cartridge (101) that includes components similar to cartridge (37) described above. Cartridge (101) includes material (114) in tape form and is disposed over exemplary firing bar (103) in lower jaw (16) of end effector (12) described above. Firing bar (103) is similar to firing bar (14), described above. FIG. 9 shows firing bar (103) as including a distal blade (100) with a top surface (102) terminating in an upper tip (104). Firing bar (103) also includes an elongate proximal portion (106) extending from distal blade (100). Top edge (108) of elongate proximal portion (106) includes notch (110). Notch (110) is configured to receive intermediate portion (112) of material (114) disposed between and connecting first and second spools (116, 118) of material (114). Spools (116, 118) of material (114) may be resiliently biased to prevent premature unraveling of material (114) from spools (116, 118).

Material (114) may be comprised of a hemostatic agent and/or various other materials, as described above. As firing bar (103) moves distally in the direction of arrow (A) through vertical slot (99) defined in upper deck (105) of cartridge (101), firing bar (103) snags and pulls material (114) distally forward while unraveling material (114) from spools (116, 118) as shown in FIG. 8. Firing bar (103) ultimately releases material (114) onto tissue severed by blade (100). Additionally or alternatively, a wedge sled, similar to wedge sled (41) described above, may attach to material (114) and pull material (114) distally forward as firing bar (103) is advanced distally.

Tissue is severed by firing bar (103) in a similar manner to how firing bar (14) severs tissue, as described above. Top edge (108) is disposed above top surfaces of spools (116, 118) such that when material (114) is driven forward by firing bar (103), layers of material (114) on either side of firing bar (103) will not come in contact with one another to stick together.

Cartridge (101) includes first and second knives (120, 122) disposed at distal end (124) of slot (99). As firing bar (103) fires distally past knives (120, 122), knives (120, 122) slice through material (114) allowing intermediate portion (112) of material (114) to be removed from notch (110) of firing bar (103). This allows firing bar (103) to return to an original position, shown in FIG. 7, without retaining a substantial portion of material (114). After cartridge (101) is used, a user may reload a new cartridge and repeat the above described process.

B. Side Notch on Firing Bar Versions

Figure 10:
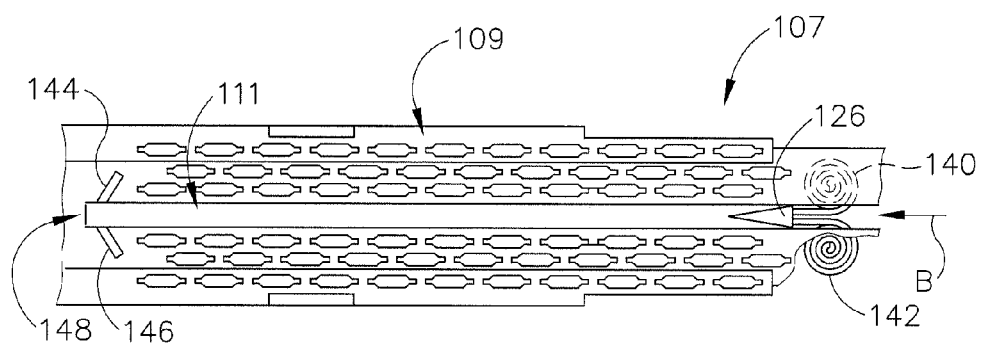
FIG. 10 depicts a plan view of an exemplary alternative version of a removable cartridge of the end effector of FIG. 2 and an exemplary firing bar with an adjunct material connected to the firing bar, with the firing bar in a first position.
Figure 11:
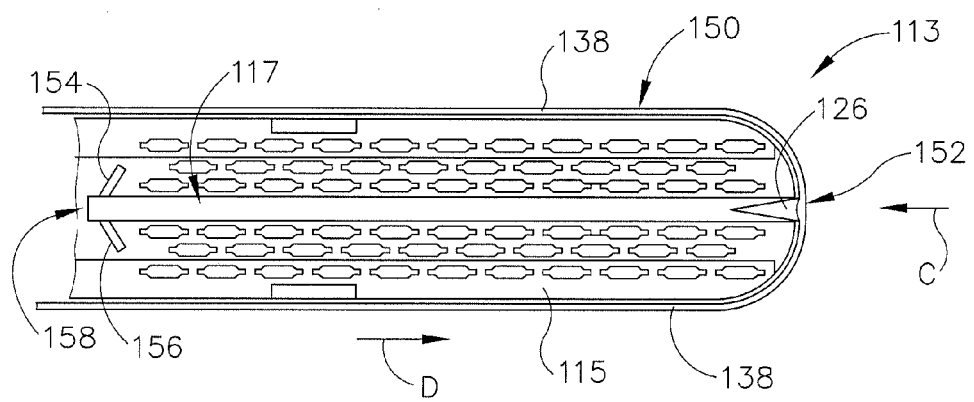
FIG. 11 depicts a plan view of yet another exemplary alternative version of a removable cartridge of the end effector of FIG. 2 and an exemplary firing bar with an adjunct material connected to the firing bar, with the firing bar in a first position.
Figure 12:
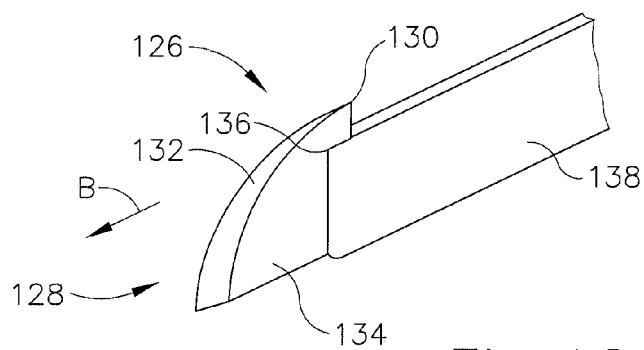
FIG. 12 depicts a fragmentary, perspective view of the adjunct material of either FIG. 10 or FIG. 11 connected to an exemplary firing bar via an elongated side notch in the firing bar.

FIGS. 10-11 show other exemplary cartridges (107, 113) that are configured for receipt in lower jaw (16). Cartridges (107, 113) further include portions to receive a firing bar (126), which is similar in operation to firing bar (14) described above with respect to cartridge (37). Referring to FIG. 12, firing bar (126) includes distal blade (128) terminating in upper tip (130). An elongate side notch (136) is disposed below top edge (132) and on or through opposite sides (134) of firing bar (126) and is configured for receipt of material (138) when exemplary cartridges (107, 113) are disposed over firing bar (126) in a first position, and as described below.

1. Spool Version

FIG. 10 shows cartridge (107) including material (138) in tape form as part of first and second spools (140, 142) disposed below deck (109). When cartridge (107) is inserted into lower jaw (16), material (138) from the inner ends of spools (140, 142) attaches to sides (134) of firing bar (126) through notch (136). For instance, cartridge (107) may be inserted into a lower jaw (16) at an angle sufficient to enable material (138) spanning between spools (140, 142) to pass under firing bar (126) and into notch (136). Such material (138) may then be retained in notch (136) as cartridge (107) is snapped into place. Alternatively, top edge (132) may include a slot communicating with notch (136), enabling material (138) to enter notch (136) from the top side of firing bar (126). In either case, when firing bar (126) is distally fired in the direction of arrow (B), material (138) from spools (140, 142) is unraveled and distally fired along with firing bar (126) until firing bar (126) reaches knives (144, 146) at distal end (148) of slot (111) of deck (109). Slot (111) is similar in structure and operation to slot (49), described above. Knives (144, 146) then act to sever material (138) from sides (134) of firing bar (126) so that firing bar (126) may return to its original position without retaining a substantial portion of material (138). Additionally, material (138) will be released onto the severed portion of tissue (90) when firing bar (126) severs tissue (90) in a manner similar to how firing bar (14) severs tissue (90), as described above.

Figure 16:
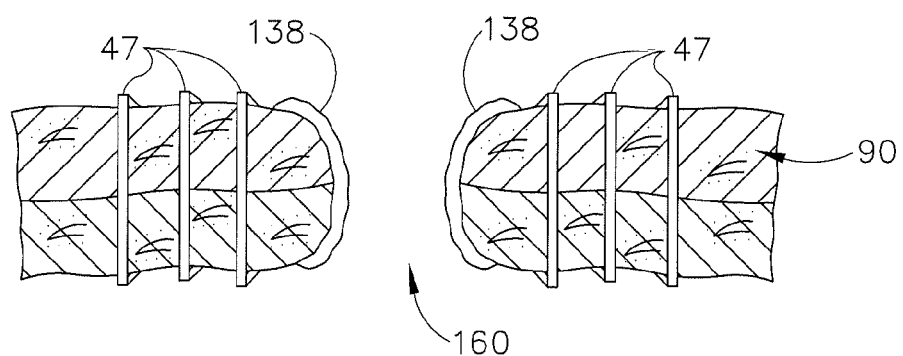
FIG. 16 depicts a cross-sectional view of adjunct material deposited as a tissue repair composition onto severed tissue.

FIG. 16 shows an example of material (138) released onto severed edges of tissue (90) that has been stapled with staples (47) from end effector (12). In particular, the severed edges of tissue (90) form a cut line (160). Material (138) is shown as deposited on tissue (90) on either sides of cut line (160), which is a line substantially aligned with slot (111) of cartridge (107) when end effector (12) including cartridge (107) operates to sever tissue (90) with firing bar (126). It should be understood that use of the various other adjunct material examples described herein may yield results appearing similar to those shown in FIG. 16.

2. Surround Version

FIG. 11 shows cartridge (113) with strips of material (138) that include surrounding portions (150). Surrounding portions (150) movably surround the outer periphery of deck (115) of cartridge (113). When cartridge (113) is inserted into lower jaw (16), material (138) from intermediate portion (152) of surrounding portion (150) is inserted into notch (136) of firing bar (126). When firing bar (126) is distally fired in the direction of arrow (C) along slot (117), which is similar to slot (111) described above, material (138) from surrounding portion (150) is snagged and distally fired along with firing bar (126), pulling material from surrounding portion (150) in the direction of arrow (D) until firing bar (126) reaches knives (154, 156) at distal end (158) of slot (111) of deck (109). Knives (154, 156) sever material (138) from firing bar (126) in a manner similar to knives (144, 146) of cartridge (107) described above. Similarly, material (138) will be released onto the severed portion of tissue (90) when firing bar (126) severs tissue (90).

C. Knife Slots Version

Figure 13:
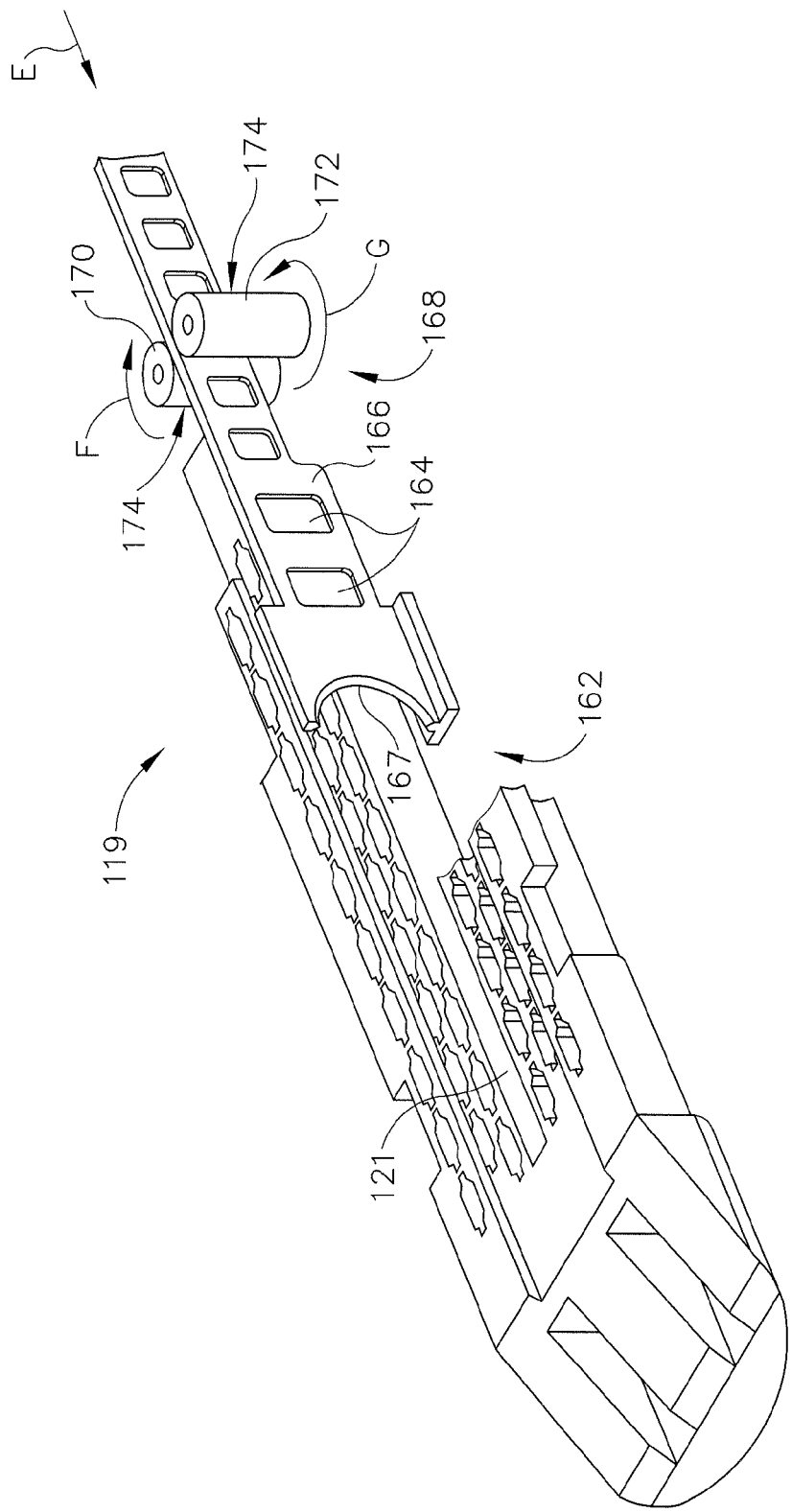
FIG. 13 depicts a perspective view of another exemplary removable cartridge of the end effector of FIG. 2 and an exemplary firing bar with an adjunct material being deposited onto the firing bar via a first version of an adjunct applicator, with the firing bar being fired through the cartridge.

FIG. 13 shows another exemplary cartridge (119), which is similar to cartridge (37) described above, except as set forth below. Cartridge (119) includes an adjunct applicator configured to dispose a hemostatic material or adjunct and/or any other suitable material onto a firing bar (162). Firing bar (162) of this example includes a series of notches (164) along a portion of its length, on opposite sides (166). Various examples of adjunct applicators that cooperate with notches (164) will be described below, while other examples will be apparent to those of ordinary skill in the art in view of the teachings herein. It should be understood that notches (164) may comprise recesses that do not pass fully from one side (166) to the other side (166). In addition or in the alternative, notches (164) may comprise openings providing complete passage from one side (166) on through to the other side (166).

1. Roller Version

Cartridge (119) may include a first version of adjunct applicator (168). FIG. 13 shows applicator (168) comprising rollers (170, 172) configured to rotatably abut against opposite sides (166) of firing bar (162). When firing bar (162) is distally advanced in the direction of arrow (E) through vertical slot (121) of cartridge (119), leading edge (167) of firing bar (162) may sever material (174) between rollers (170, 172). Alternatively, firing bar (162) may simply pass along rollers (170, 172) without severing anything between rollers (170, 172). As firing bar (162) continues to advance distally, material (174) will roll against and coat sides (166) of firing bar (162) through a wicking action. Particularly, rollers (170, 172) will respectively roll in the directions of arrows (F, G) to release material (174) from rollers (170, 172) into notches (164). Such an action coats sides (166) of firing bar (162) in a manner similar to how a felt tip pen might apply and release ink onto paper, for example. Notches (164) retaining material (174) deposit material (174) via another wicking action to a top and button of a cut line, such as cut line (160) shown in FIG. 16, when firing bar (162) severs tissue (90) in a manner described above for end effector (12). Firing bar (162) thus ultimately applies material (174) to cut line (160) while simultaneously severing tissue (90) to create cut line (160).

2. Ampoule Version

Figure 14:
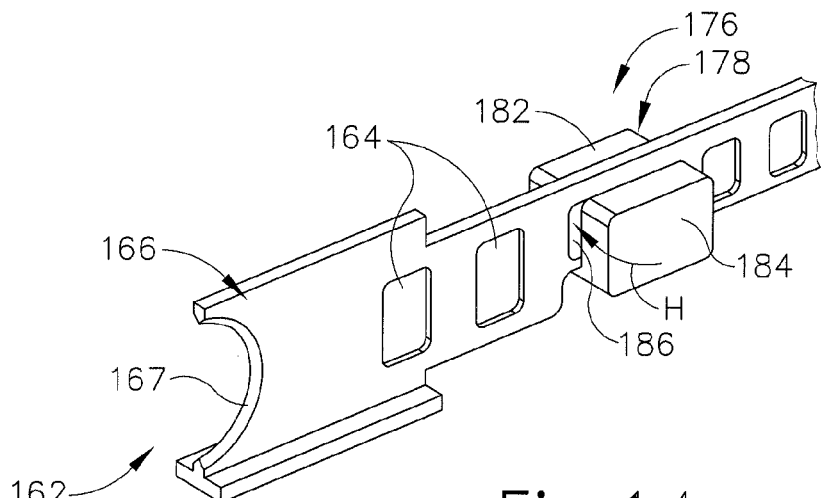
FIG. 14 depicts a fragmentary, perspective view of an alternative second version of an adjunct applicator for the cartridge of FIG. 13.

As another merely illustrative example, cartridge (119) may include a second version of adjunct applicator (176), which is shown in FIG. 14. Applicator (176) of this example comprises an ampoule (178), which may be comprised of plastic or any other suitable material. Ampoule (178) is disposed along a proximal end of vertical slot (121) of cartridge (119). When cartridge (119) is disposed in lower jaw (16) of end effector (12), upper edge (180) of firing bar (162) severs ampoule (178) into first and second portions (182, 184) on opposite sides (166) of firing bar (162). Alternatively, when cartridge (119) is disposed in lower jaw (16) of end effector (12), leading edge (167) of firing bar (162) advances distally to sever ampoule (178) into first and second portions (182, 184) on opposite sides (166) of firing bar (162). As firing bar (162) advances distally through slot (121) and through the severed ampoule (178), agent (186) flows from ampoule (178) out onto sides (166) of firing bar (162) in a path depicted by arrow (H) for retention in notches (164) of firing bar (162). Agent (186) is thereby applied via the firing of firing bar (162) to a cut line, such as cut line (160) shown in FIG. 16, when firing bar (162) severs tissue (90) in a manner described above for end effector (12).

3. Spring-Biased Gel Block Version

Figure 15:
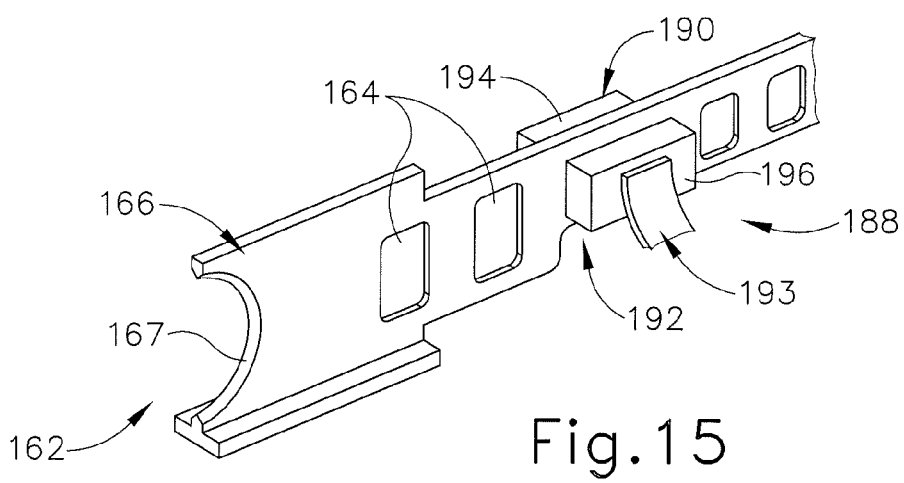
FIG. 15 depicts a fragmentary, perspective view of an alternative third version of an adjunct applicator for the cartridge of FIG. 13.

As yet another merely illustrative example, cartridge (119) may include a third version of adjunct applicator (188), which is shown in FIG. 15. Applicator (188) of this example comprises a gel block (190) of agent (192) with a pair of springs (193) located on opposite sides of gel block (190) to bias block (190) against sides (166) of firing bar (162). Block (190) is disposed along a proximal end of vertical slot (121) of cartridge (119). When cartridge (119) is disposed in lower jaw (16) of end effector (12), upper edge (180) of firing bar (162) severs block (190) into block portions (194, 196) on opposite sides (166) of firing bar (162). Alternatively, when cartridge (119) is disposed in lower jaw (16) of end effector (12), leading edge (167) of firing bar (162) advances distally to sever block (190) into first and second portions (194, 196) on opposite sides (166) of firing bar (162). As yet another alternative, first and second portions (194, 196) may be preformed as two separate blocks (190) such that firing bar (162) does not sever block (190). In any of these examples, as firing bar (162) advances distally through slot (121), agent (192) retained in block (190) is transferred from block portions (194, 196) onto sides (166) of firing bar (162) for retention in notches (164) of firing bar (162). Springs (193) press against outer sides of each of block portions (194, 196) to bias inner sides of block portions (194, 196) against respective opposite sides (166) of firing bar (162) as firing bar (162) advances distally through slot (121) of cartridge (119). Agent (192) is thereby applied via the firing of firing bar (162) to a cut line, such as cut line (160) shown in FIG. 16, when firing bar (162) severs tissue (90) in a manner described above for end effector (12).

It should be understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Versions of the devices described above may have application in conventional medical treatments and procedures conducted by a medical professional, as well as application in robotic-assisted medical treatments and procedures.

Versions of described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument apparatus comprising:
 (a) a handle portion;
 (b) a shaft housing a firing bar;
 (c) an end effector comprising an anvil, a lower jaw, and a stapling and severing assembly responsive to a longitudinal closing motion produced by the handle portion and the shaft; and
 (d) a removable cartridge, wherein the lower jaw is configured to receive the cartridge, the cartridge comprising:
  (i) a housing,
  (ii) a plurality of staples disposed in the housing,
  (iii) a deck disposed over the plurality of staples, the deck defining a plurality of apertures, each aperture being substantially disposed over each staple, and
  (iv) a biocompatible material, wherein the firing bar is operable to apply the biocompatible material to tissue while the stapling and severing assembly simultaneously severs and drives staples into the tissue, wherein the firing bar includes a notch configured to receive the biocompatible material.

2. The apparatus of claim 1, wherein the biocompatible material is disposed on or beneath the deck of the cartridge at a proximal end of the cartridge.

3. The apparatus of claim 1, wherein the biocompatible material is wrapped about a pair of spools.

4. The apparatus of claim 3, wherein the spools are resiliently biased.

5. The apparatus of claim 3, wherein the biocompatible material wrapped about the spools is configured to advance when the firing bar advances through a slot of the deck of the cartridge in response to the longitudinal closing motion produced by the handle portion and the shaft.

6. The apparatus of claim 5, further comprising a pair of knives positioned at a distal end of the slot of the deck of the cartridge.

7. The apparatus of claim 6, wherein the knives are configured to sever the biocompatible material when the biocompatible material reaches the distal end of the slot.

8. The apparatus of claim 1, wherein when the biocompatible material comprises a tape, wherein a notch in the firing bar is configured to receive the tape.

9. The apparatus of claim 1, wherein an area proximal to a leading edge of the firing bar is configured to receive the biocompatible material.

10. The apparatus of claim 9, further comprising a pair of rollers configured to release the biocompatible material onto notches on side surfaces of the firing bar when the firing bar advances distally.

11. The apparatus of claim 9, further comprising an ampoule housing the biocompatible material, wherein the leading edge of the firing bar is configured to sever the ampoule when the firing bar advances distally to release the biocompatible material into notches on side surfaces of the firing bar.

12. The apparatus of claim 9, wherein the biocompatible material comprises a spring-biased gel block, wherein the leading edge of the firing bar is configured to advance distally past the gel block when the firing bar advances distally to release the biocompatible material into notches on side surfaces of the firing bar.

13. The apparatus of claim 12, wherein the spring-biased gel block comprises a pair of blocks resiliently biased against opposite sides of the firing bar.

14. The apparatus of claim 12, wherein the spring-biased gel block comprises a severable block, and wherein the leading edge of the firing bar is configured to advance distally to sever the severable block into a pair of block portions such that the biocompatible material is released from severed areas of the pair of block portions into notches on side surfaces of the firing bar.

15. A method of releasing material from a surgical instrument, the surgical instrument including an end effector, a handle portion, and a shaft housing a firing bar, the end effector including a lower jaw and an anvil, the lower jaw being configured to receive a removable cartridge, the cartridge including a deck having a vertical slot, the instrument further including a stapling and severing assembly responsive to a longitudinal closing motion produced by the handle portion and the shaft, the stapling and severing assembly including the firing bar, the method comprising the steps of:
    (a) inserting the cartridge comprising a biocompatible material in the lower jaw of the end effector such that the biocompatible material is retained within a notch in the firing bar when the firing bar is in a first position; and
    (b) producing the longitudinal closing motion to advance the firing bar of the stapling and severing assembly through the vertical slot of the deck of the cartridge to a second position, such that the advancement of the firing bar concurrently advances the retained biocompatible material.

16. The method of claim 15, further comprising the step of:
    (a) severing the advanced retained biocompatible material by a pair of knives positioned at a distal end of the vertical slot of the deck of the cartridge.

17. The method of claim 16, further comprising the step of:
    (a) urging the firing bar to the first position upon removal of the longitudinal closing motion produced by the handle portion and the shaft.

18. A surgical instrument comprising:
    (a) a handle portion and a shaft, the shaft housing a firing bar;
    (b) a stapling and severing assembly responsive to a longitudinal closing motion produced by the handle portion and the shaft,
    (c) a staple cartridge;
    (d) an end effector connected to the handle portion, the end effector comprising an anvil and a lower jaw, the lower jaw being configured to receive the staple cartridge;
    (e) a plurality of staples disposed in a housing of the staple cartridge, the anvil being configured to form the staples in response to the longitudinal closing motion; and
    (f) a biocompatible material, wherein the biocompatible material is disposed on or in the staple cartridge;
    wherein the firing bar comprises a plurality of notches, wherein the firing bar is operable to move between the anvil and the cartridge, and wherein the notches are configured to retain portions of the biocompatible material.

19. The instrument of claim 18, wherein the firing bar is operable to sever the biocompatible material, and wherein the notches are configured to retain portions of the severed material, wherein the biocompatible material comprises one or more of adhesives, sealants, healing agents, or antimicrobials.

* * * * *